(12) United States Patent
Mannino et al.

(10) Patent No.: US 8,273,887 B2
(45) Date of Patent: *Sep. 25, 2012

(54) PROCESSES FOR SYNTHESIS OF OPIATE ALKALOID DERIVATIVES

(75) Inventors: Anthony Mannino, Maryland Heights, MO (US); James Zdrodowski, Alexandria, VA (US)

(73) Assignee: Mallinckrodt LLC, Hazelwood, MO (US)

( * ) Notice: Subject to any disclaimer, the term of this patent is extended or adjusted under 35 U.S.C. 154(b) by 451 days.

This patent is subject to a terminal disclaimer.

(21) Appl. No.: 12/586,874

(22) Filed: Sep. 29, 2009

(65) Prior Publication Data

US 2010/0081816 A1 Apr. 1, 2010

Related U.S. Application Data

(60) Provisional application No. 61/194,779, filed on Sep. 30, 2008.

(51) Int. Cl.
*C07D 489/12* (2006.01)
*C07D 489/02* (2006.01)
(52) U.S. Cl. .......................................... 546/39; 546/44
(58) Field of Classification Search .................. 546/39, 546/40, 44
See application file for complete search history.

(56) References Cited

U.S. PATENT DOCUMENTS

| | | | |
|---|---|---|---|
| 3,763,167 A | 10/1973 | Hydro | |
| 5,633,259 A | 5/1997 | Qin et al. | |
| 5,849,915 A | 12/1998 | Kim et al. | |
| 2003/0194420 A1 | 10/2003 | Holl et al. | |
| 2008/0045715 A1 | 2/2008 | Mitchell et al. | |

FOREIGN PATENT DOCUMENTS

| | | |
|---|---|---|
| CN | 1939920 | 4/2007 |
| HU | 76478 | 9/1997 |
| WO | WO 03/024972 | 3/2003 |

OTHER PUBLICATIONS

Bentley et al., "Novel Analgesics and Molecular . . . ", Journal of the American Chemical Society, 89(13), 1967, pp. 3267-3273.
Bentley et al., "Novel Analgesics and Molecular Rearrangements in the Morphine-Thebaine Group . . . ", Journal of the American Chemical Society, 1967, 89(13), pp. 3281-3292.
Grundt et al., "Formic Acid Catalyzed Rearrangement of Thevinols . . . ", Helv. Chim. Acta, 86(7), 2003, pp. 2287-2298, XP 002560362.
Henderson et al., "Synthesis from Thebaine of 10-oxothebaine . . . ", J. Chem. Soc., 1994, (3), pp. 295-297.
Hori et al., "Synthesis of the novel Sulfur-Containing . . . ", Chemical and Pharmaceutical bulletin, 1984, 32(3), pp. 1268-1271.
Iwamura et al., "Synthesis of 6,14-ethenomorphines and the Cytostatic Activity of Tumor Cells", Gifu yakka Daigaku Kiyo, 2005, 54, pp. 45-50.
Leonard et al., "Determination of the Relative and Absolute Configuration . . . ", Organic Letters, 4(4), 2002, pp. 4201-4204, XP 002560364.
Leonard et al., "Determination of the Relative and Absolute Configuration . . . ", Organic Letters Supporting Information, 2002, XP 002563404.
Li et al., "Selective Demethylation Process in Synthesis of Etorphine and Hydrotorphine", Guanxi Daxue Xuebao, Ziran Kexueban, 2004, 29(3), pp. 265-268.
Ma, Sicai et al., "Improved Synthesis of Diprenorphine", Zhongguo Yixao Gongye Zazhi, 1992, 23(40, pp. 157-158.
Marton et al., "Herstellung von 6, 14-Ethenomorphinan-Derivaten", Monatshefte Fuer chemie, 125(11), 1994, pp. 1229-1239, XP 002560363.
Maxichen et al., "Synthesis of the Highly Efficient . . . ", Jingxi Huagong, 1996, 13(1), pp. 12-15.
Russell et al., "One-Pot synthesis Aids Scale-Up and Data Collection", Pharmaceutical Technology, Advanstar Communications, Inc. US, no. Nov. 1, 2003, pps. 17, 22, XP 002433225.
Valhari et al., "Formation of 6,14-endo-ethenotetrahydrothebaine . . . ", Science International, 1992, 4(1), pp. 53-58.
Wan et al., "Synthesis of an Opiate Receptor . . . ", Shangha Dixi Yixueyuan Xuebao, 1985, 12(1), pp. 25-30.
Wang et al., "Synthesis of 3-H-thienorphine", Zhongguo Xinyao Zazhi, 2004, 13(11), pp. 1012-1015.
Woudenberg et al., "Chemistry of Opium Alkaloids . . . ", Recuell des Travaux Chimiques des Pays-Bas, 1990, 109(5), pp. 353-357.

*Primary Examiner* — Charanjit Aulakh

(57) ABSTRACT

The present invention provides processes for the synthesis of opiate alkaloids. In particular, the opiate alkaloids produced by the process of the invention are typically intermediate compounds that may be utilized to produce a variety of biologically active alkaloids including buprenorphine and diprenorphine.

9 Claims, No Drawings

PROCESSES FOR SYNTHESIS OF OPIATE ALKALOID DERIVATIVES

FIELD OF THE INVENTION

The present invention generally relates to processes for the synthesis of opiate alkaloids. In particular, the present invention provides processes for the formation of opiate alkaloids that minimizes the formation of impurities and decreases reaction time.

BACKGROUND OF THE INVENTION

Thebaine is an opiate alkaloid. While thebaine is not used therapeutically itself, it can be converted industrially into a variety of therapeutically important opiate alkaloids including oxycodone, oxymorphone, nalbuphine, naloxone, naltrexone, diprenorphine, buprenorphine and etorphine. Buprenorphine, for example, is a thebaine derivative with powerful analgesia approximately twenty-five to forty times as potent as morphine, and is indicated for the treatment of moderate to severe chronic pain or for pre-operative analgesia.

Buprenorphine is made via a synthetic route that starts with the conversion of thebaine to 6,14-endo-etheno-7-α-acetyltetrahydro-thebaine. In particular, thebaine has been reacted with a dienophile (e.g., methyl vinyl ketone) in the presence of an alcohol to produce the Diels Alder product 6,14-endo-etheno-7α-acetyltetrahydro-thebaine. The Diels Alder product is then hydrogenated to produce 7-acetyl-6,14-endoethano-6,7,8,14-tetrahydrothebaine.

Several of the synthetic routes used to produce 7-acetyl-6,14-endoethano-6,7,8,14-tetrahydrothebaine present serious disadvantages. For example, U.S. Pat. No. 5,849,915 ('915 patent) describes a process for forming buprenorphine that includes reacting thebaine with an excess of methyl vinyl ketone in a Diels-Alder step. The excess unsaturated ketone is removed after the reaction by distillation under reduced pressure. The residue produced in this step is dissolved in boiling methanol, which was then cooled to produce a crystalline solid, which is filtered and washed with cool methanol, and dried under reduced pressure to produce 7-acetyl-6,14-endo-etheno tetrahydrothebaine in a yield of 92%. The 7-acetyl-6,14-endoetheno tetrahydrothebaine is then dissolved in ethanol and hydrogenated with 5% palladium on charcoal catalyst for 30 hours at room temperature and a pressure of 60 psig. After removal of the catalyst, 7-acetyl-6,14-endoethano tetrahydrothebaine is obtained at only 80% yield by recrystallization of formed product from ethanol. The product 7-acetyl-6,14-endoethano tetrahydrothebaine is then converted to buprenorphine using a series of additional reaction steps.

As illustrated by the process detailed in the '915 patent, the amount of time required to conduct the Diels-Alder reaction and the hydrogenation reaction according to prior processes is undesirably high. In addition, the requirement in the prior processes for removal of excess methyl vinyl ketone has the potentially detrimental consequences of increasing the chance of exposing workers to methyl vinyl ketone, which is a hazardous substance. Also, a relatively complex series of steps is required to recrystallize 7-acetyl-6,14-endoethano tetrahydrothebaine from the hydrogenation reaction mixture and to remove the relatively large amount of epimeric impurity formed in the process. Also, the yield of 80% in the hydrogenation step is too low.

SUMMARY OF THE INVENTION

Briefly, therefore, the present invention provides a synthetic route for the production of a morphinan comprising an alkano bridge that connects C(6) to C(14) (e.g., 7-acetyl-6,14-endoethano tetrahydrothebaine). In particular, it has been discovered that use of an aprotic solvent in the hydrogenation reaction results not only in increased product yield and purity, but it also beneficially reduces the reaction time.

One aspect of the invention encompasses a process for the preparation of a morphinan comprising an alkano bridge that connects C(6) to C(14). The process comprises contacting a morphinan comprising an alkeno bridge that connects C(6) to C(14) with an aprotic solvent and a catalyst that catalyzes hydrogen addition to the alkeno bridge to produce the morphinan comprising an alkano bridge that connects C(6) to C(14).

Yet another aspect of the invention provides a process for the preparation of a compound comprising Formula (III). The process comprises contacting a compound comprising Formula (II) with a catalyst and an aprotic solvent to form a compound comprising Formula (III) according to the following reaction scheme:

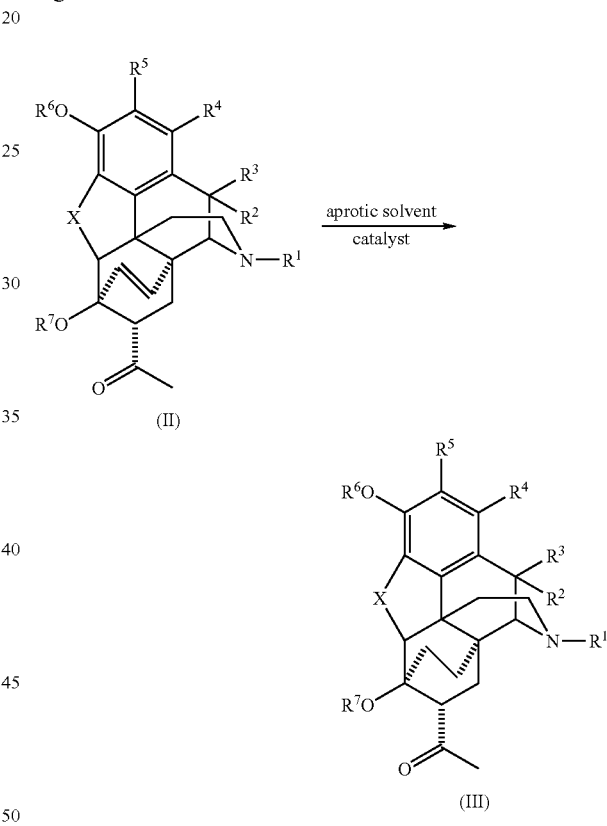

wherein:
$R^1$ and $R^8$ are independently selected from the group consisting of hydrocarbyl and substituted hydrocarbyl;
$R^2$ and $R^3$ are independently selected from the group hydrogen, hydrocarbyl and substituted hydrocarbyl;
$R^4$ and $R^5$ are independently selected from the group consisting of hydrogen, hydrocarbyl, substituted hydrocarbyl, halogen, {—}OH, {—}NH$_2$, {—}SH, {—}SR$^8$, and {—}OR$^8$;
$R^6$ and $R^7$ are independently selected from the group consisting of hydrogen, a protecting group, hydrocarbyl, and substituted hydrocarbyl; and
X is a heteroatom.

Another aspect of the invention encompasses a process for the preparation of a compound comprising Formula (III). The process comprises a first reaction that comprises contacting a compound comprising Formula (I) with a solvent and a dienophile to form a compound comprising Formula (II). In a second reaction, the compound comprising Formula (II) is contacted with a catalyst and an aprotic solvent to form a compound comprising Formula (III) according to the following reaction scheme:

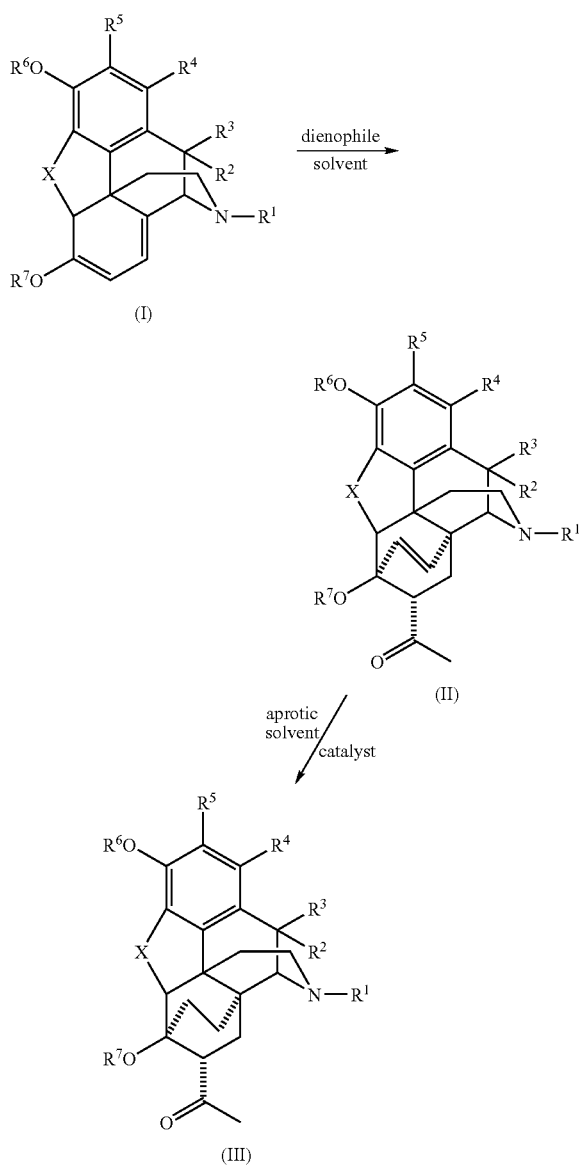

wherein:

$R^1$ and $R^8$ are independently selected from the group consisting of hydrocarbyl and substituted hydrocarbyl;

$R^2$ and $R^3$ are independently selected from the group hydrogen, hydrocarbyl and substituted hydrocarbyl;

$R^4$ and $R^5$ are independently selected from the group consisting of hydrogen, hydrocarbyl, substituted hydrocarbyl, halogen, {—}OH, {—}NH$_2$, {—}SH, {—}SR$^8$, and {—}OR$^8$;

$R^6$ and $R^7$ are independently selected from the group consisting of hydrogen, a protecting group, hydrocarbyl, and substituted hydrocarbyl; and X is a heteroatom.

Additional aspects and iterations of the invention are described in more detail below.

DETAILED DESCRIPTION OF THE INVENTION

The invention provides an efficient synthetic route for the production of opiate alkaloids in a one-pot or two-pot process via a cycloaddition reaction between an opiate compound comprising a conjugated diene and a dienophile, followed by hydrogenation of the resulting product to form an opiate alkaloid. In particular, it has been discovered that use of an aprotic solvent in the hydrogenation reaction results not only in increased product yield and purity, but it also beneficially reduces the reaction time. For example, it has been discovered that use of an aprotic solvent (e.g., isopropyl acetate) compared to a protic solvent (i.e., acetic acid) in the hydrogenation reaction reduces the overall reaction time by over fifty percent in several iterations of the invention. The process of the invention also substantially eliminates the need for workers' to handle the hazardous dienophile (e.g., methyl vinyl ketone) used as a reagent in the cycloaddition reaction. Toward this end, in certain iterations of the invention, the overall reaction (i.e., cycloaddition and hydrogenation) may be done in a one-pot process, thus eliminating the need to remove the dienophile after the cycloaddition reaction. Moreover, if the dienophile is methyl vinyl ketone most of it is reduced to the much less toxic ketone-2 during the hydrogenation reaction. It has also been discovered that the addition of an alkane while the hydrogenation reaction is cooling results in crystallization of the alkaloid product in a substantially pure form. The alkaloids produced by the process of the invention are typically intermediate compounds that may be utilized to produce a variety of biologically active alkaloids including buprenorphine and diprenorphine.

For the purposes of convenience, the first reaction step in accordance with exemplary iterations of the process involves a cycloaddition reaction between an opiate compound comprising a conjugated diene and a dienophile. This reaction is generally known as a Diels Alder reaction and results in the production of an opiate alkaloid. The second reaction step is sometimes referred to herein for convenience as the hydrogenation reaction. The Diels Alder reaction is described in section (I) below and the hydrogenation reaction is described in section (II) below.

As will be appreciated by a skilled artisan, the Diels Alder reaction and hydrogenation reaction may be conducted in separate vessels or in the same vessel without departing from the scope of the invention. For example, although it is contemplated that in certain embodiments the Diels-Alder reaction and the hydrogenation reaction may each be conducted batch-wise in a separate reaction vessel, it is also contemplated that in certain preferred embodiments these reactions may be conducted batch-wise but in the same vessel, or in a continuous or semi continuous mode. In fact, one advantage of certain embodiments of the present invention is that the present methods are more readily adapted than many of the prior methods for use in connection with continuous or semi continuous processes. Thus it will be appreciated that the description of each of the steps in separate sections of the present application is for the purposes of convenience but not for any necessarily limiting purpose.

(I) Synthesis of Compounds Comprising Formula (II): Diels Alder Reaction

The process of the invention may comprise a cycloaddition reaction between an opiate compound comprising a conjugated diene, namely a compound comprising Formula (I), and a dienophile to produce an opiate alkaloid comprising Formula (II). For purposes of illustration, Reaction Scheme 1 depicts production of compound comprising Formula (II) in accordance with one aspect of the invention:

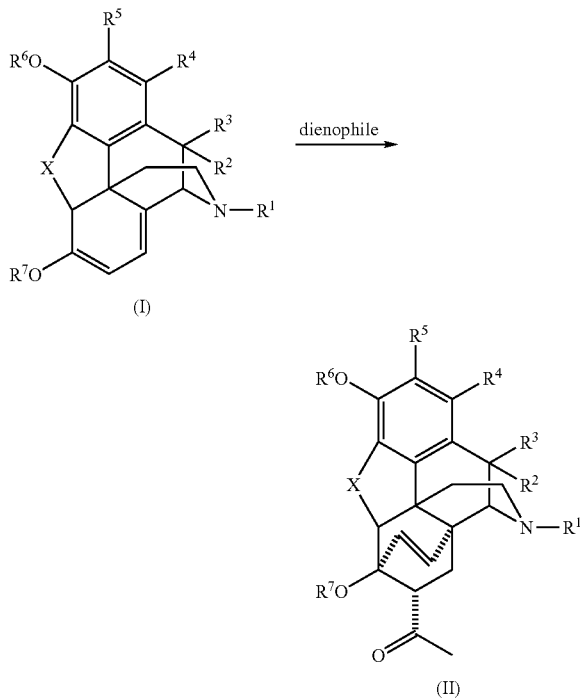

(I)

(II)

wherein:
- $R^1$ and $R^8$ are independently selected from the group consisting of hydrocarbyl and substituted hydrocarbyl;
- $R^2$ and $R^3$ are independently selected from the group hydrogen, hydrocarbyl and substituted hydrocarbyl;
- $R^4$ and $R^5$ are independently selected from the group consisting of hydrogen, hydrocarbyl, substituted hydrocarbyl, halogen, {—}OH, {—}$NH_2$, {—}SH, {—}$SR^8$, and {—}$OR^8$;
- $R^6$ and $R^7$ are independently selected from the group consisting of hydrogen, a protecting group, hydrocarbyl, and substituted hydrocarbyl; and
- X is a heteroatom.

In one exemplary embodiment, the compound comprising Formula (II) is 6,14-endo-etheno-7-acetyltetrahydro-thebaine or a derivative of 6,14-endo-etheno-7-acetyltetrahydro-thebaine comprising Formula (IIa):

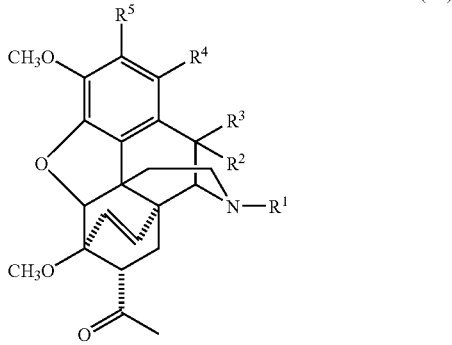

(IIa)

wherein:
$R^1$, $R^2$, $R^3$, $R^4$, and $R^5$ are as defined for compounds comprising Formula (II). In an exemplary embodiment, the compound of Formula (IIa) is 6,14-endo-etheno-7-acetyltetrahydro-thebaine (i.e., when $R^1$ is methyl, and $R^2$, $R^3$, $R^4$, and $R^5$ are hydrogen).

In yet another exemplary embodiment, the compound comprising Formula (II) is 6,14-endo-etheno-7-acetyltetrahydro-oripavine or a derivative of 6,14-endo-etheno-7-acetyltetrahydro-oripavine comprising Formula (IIb):

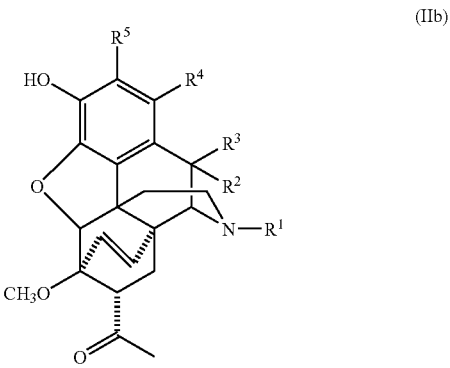

(IIb)

wherein:
$R^1$, $R^2$, $R^3$, $R^4$, and $R^5$ are as defined for compounds comprising Formula (II). In an exemplary embodiment, the compound of Formula (IIb) is 6,14-endo-etheno-7-acetyltetrahydro-oripavine (i.e., when $R^1$ is methyl, and $R^2$, $R^3$, $R^4$, and $R^5$ are hydrogen).

The process commences with formation of a reaction mixture by combining a compound comprising Formula (I), with a dienophile. The reaction is generally carried out in the presence of a solvent. A variety of compounds having Formula (I) are suitable for use in the process. In one iteration of the process, for the compound having Formula (I), $R^1$ is an alkyl or substituted alkyl, $R^2$, $R^3$, $R^4$, and $R^5$ are hydrogen, and X is oxygen. In an alternative iteration, $R^6$ is methyl, and $R^7$ is methyl. In still another alternative iteration, $R^6$ is hydrogen and $R^7$ is methyl.

In one exemplary embodiment of the process, the compound comprising Formula (I) is thebaine or a thebaine derivative comprising Formula (Ia):

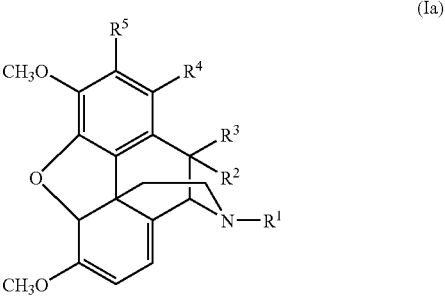

(Ia)

wherein:
$R^1$, $R^2$, $R^3$, $R^4$, and $R^5$ are as defined for compounds comprising Formula (I). In an exemplary embodiment, the compound of Formula (Ia) is thebaine (i.e., when $R^1$ is methyl, and $R^2$, $R^3$, $R^4$, and $R^5$ are hydrogen). In the process, when the compound of Formula (Ia) comprises thebaine then the resulting product is 6,14-endo-etheno-7-acetyltetrahydro-thebaine.

In an alternative embodiment of the process, the compound comprising Formula (I) is oripavine or an oripavine derivative comprising Formula (Ib):

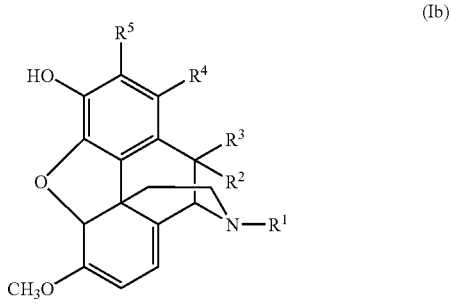

(Ib)

wherein:

$R^1$, $R^2$, $R^3$, $R^4$, and $R^5$ are as defined for compounds comprising Formula (I). In an exemplary embodiment, the compound of Formula (Ib) is oripavine (i.e., when $R^1$ is methyl, and $R^2$, $R^3$, $R^4$, and $R^5$ are hydrogen). In the process, when the compound of Formula (Ib) comprises oripavine then the resulting product is 6,14-endo-etheno-7-acetyltetrahydro-oripavine.

In addition to a compound comprising Formula (I), the reaction mixture also comprises a dienophile. Typically, the dienophile is an α,β-unsaturated electron deficient dienophile. An exemplary dienophile is methyl vinyl ketone. Other suitable dienophiles include but are not limited to maleic anhydride, methyl acrylate, diethyl fumarate, benzoquinone, acetylene, 4-phenyl-1,2,4-triazolin-3,4-dione, and 2-methylpropenal.

The reaction mixture, as detailed herein, also typically includes a solvent. As used herein, the term "solvent" refers to any one or more compounds that are capable of establishing a substantially continuous phase within which the above noted reactants are carried, such as by suspension, solution or the like. In certain preferred embodiments, the solvent is generally a liquid at room temperature and has the capacity of solvating at least a portion of, and preferably substantially all of, the reactants mentioned herein under reaction conditions. In particularly preferred embodiments, the solvent is a solvent for the reactants and even more preferably includes an acetate moiety. The solvent is preferably selected from the group consisting of isopropyl acetate, ethyl acetate, toluene, and combinations of two or more of these. In highly preferred embodiments the solvent comprises, and even more preferably consists essentially of, isopropyl acetate. Although it is contemplated that other solvents, such as methanol, ethanol, isopropanol, tetrahydrofuran, acetonitrile, dimethylformamide and the like, may be used in combination with the preferred solvents mentioned above.

In general, it is contemplated that the temperature of the Diels-Alder reaction step may vary widely within the scope of the present invention. In certain highly preferred embodiments the temperature of the reaction is preferably from about 50° C. to about 110° C., and more preferably from about 70° C. to about 100° C., and even more preferably in certain embodiments about 80° C.

It is also generally contemplated that the pressure of the Diels-Alder reaction step may vary widely within the scope of the present invention. In certain highly preferred embodiments the pressure of the reaction is maintained in the range of from about 5 psig to about 50 psig, and more preferably from about 20 psig to about 40 psig, and even more preferably in certain embodiments at about 30 psig.

With respect to reaction times, it is also contemplated that this reaction condition may be varied over a relatively wide range, depending upon the particular circumstances of each application. Nevertheless, applicants believe that certain aspects of the present invention permit the use of relatively short reaction times to produce relatively high yields of the desired components. Thus, in certain exemplary embodiments, it is preferred that the reaction time of the Diels-Alder reaction, particularly in the case of batch-wise processing, is for a time of from about 2 hours to about 8 hours, more preferably for a time of from about 3 hours to about 5 hours, and even more preferably about 4 hours.

It is contemplated also that the yield of the desired reaction product from the Diels-Alder reaction step may vary widely within the scope of the present invention. However, in certain highly preferred embodiments, particularly and especially those in which the opiate alkaloid starting material is thebaine and the dienophile is methyl vinyl ketone, the yield of desired reaction product, including preferably 7-acetyl-6,14-endoetheno-6,7,8,14-tetrahydrothebaine is at least about 88%, more preferably at least about 93%, and even more preferably at least about 95%.

The relative proportions of the reactants and the solvent present in the Diels-Alder reaction may also vary widely and remain within the broad scope of the present invention. In preferred embodiments, dienophile, such as methyl vinyl ketone, is present in a molar excess relative to the opiate alkaloid starting material, and even more preferably in an amount that is at least about 2.2 times the stoichiometric amount, and even more preferably at least about 1.2 times the stoichiometric amount. In certain preferred embodiments, the weight ratio of thebaine to methyl vinyl ketone introduced into the reaction vessel is from about 1:2 to about 4:1, more preferably from about 1.5:1 to about 2.5:1 and even more preferably from about 1.7:1 to about 2.2:1. In addition, it is contemplated that the amount of the solvent present will be readily determined by those skilled in the art in view of the particular needs of the reaction in each specific case. However, in preferred embodiments, the weight ratio of thebaine to solvent, preferably isopropyl acetate, introduced into the reaction vessel is from about 1:1.5 to about 1:8, more preferably from about 1:2 to about 1:5, and even more preferably from about 1:2.3 to about 1:2.9.

It is optional, but preferred, that the reaction product, preferably containing the desired Diels-Alder adduct in relatively high yield as described herein, is subjected to a filtration step which eliminates at least a portion, and preferably at least a substantial portion, of any unwanted solid or semi-solid byproducts produced during the Diels-Alder reaction. In preferred embodiments, the filtration step comprises introducing a filter medium, such as preferably diatomaceous earth or similar material, into the reaction product mixture followed by separation of the filter aid to obtain a filtrate comprising the desired Diels-Alder adduct.

In general, it is contemplated that the reaction product will also include one or more isomers of the desired Diels-Alder adduct, un-reacted dienophilic material, including particularly methyl vinyl ketone, and at least a substantial portion of the solvent, including preferably isopropyl acetate. While applicants do not intend to be necessarily bound by any specific theory, it is believed that at least some of the advantages of preferred embodiments of the present invention derive from the relatively unique character of the reaction product from the Diels-Alder reaction, particularly insofar as such reaction product can be introduced directly into the subsequent hydrogenation step, without the need for isolation of the desired Diels-Alder adduct from these other materials contained in the reaction product mixture. In fact, applicants believe, without necessarily being bound, that the presence of the particular solvents of the present invention, particularly isopropyl acetate, enhance the yield of the subsequent hydrogenation step, which is described in more detail below.

(II) Synthesis of Compounds Comprising Formula (III): Hydrogenation Reaction

An important aspect of certain embodiments of the present invention involves the step of hydrogenating an endoalkeno compound, such as a compound comprising Formula (II), in the presence of an aprotic solvent to produce a reaction product comprising a hydrogenated derivative of the endoalkeno compound. In preferred embodiments at least a portion of the crude reaction product filtrate of the Diels-Alder reaction as described above, comprising epimers and other byproducts, unreacted methyl vinyl ketone, and solvent, form at least a portion of the reaction mixture for the hydrogenation reaction, thereby converting at least a portion of the endoalkeno compound, preferably an endoetheno compound, and even more preferably a compound of Formula (II), to the desired endoalkano compound, preferably a desired endoethano product, and even more preferably a compound of Formula (III). For purposes of illustration, the hydrogenation reaction is depicted in Reaction Scheme 2:

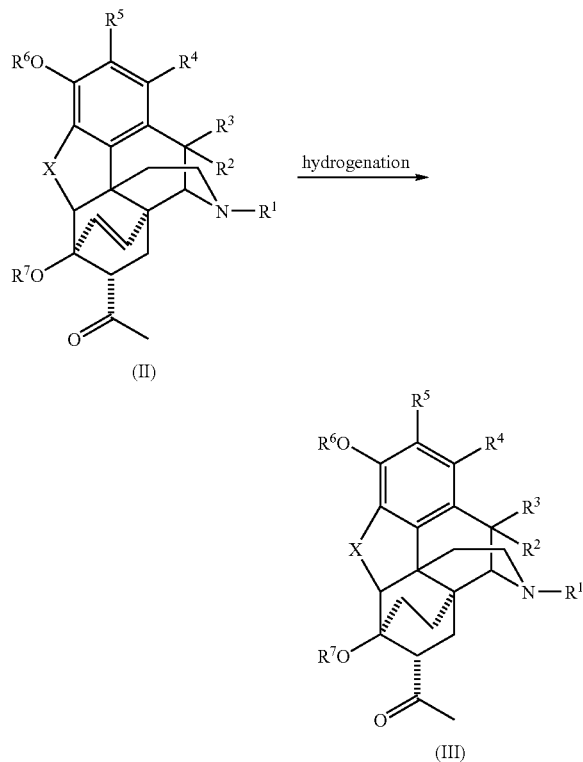

wherein:
$R^1$, $R^2$, $R^3$, $R^4$, $R^5$, $R^6$, $R^7$, and X are as described above for compounds having Formula (II).

(a) Hydrogenation Reaction Mixture

The process commences with formation of a hydrogenation reaction mixture by combining a compound comprising Formula (II), with a catalyst in the presence of an aprotic solvent. A variety of compounds having Formula (II) are suitable for use in the process. In one iteration of the process, for the compound having Formula (II), $R^1$ is an alkyl or substituted alkyl, $R^2$, $R^3$, $R^4$, and $R^5$ are hydrogen, and X is oxygen. In an alternative iteration, $R^6$ is methyl, and $R^7$ is methyl. In still another alternative iteration, $R^6$ is hydrogen and $R^7$ is methyl. In an exemplary embodiment, the compound comprising Formula (II) is 6,14-endo-etheno-7-acetyltetrahydro-thebaine or a derivative of 6,14-endo-etheno-7-acetyltetrahydro-thebaine comprising Formula (IIa) as detailed in Section (I). In an alternative exemplary embodiment, the compound comprising Formula (II) is 6,14-endo-etheno-7-acetyltetrahydro-oripavine or a derivative of 6,14-endo-etheno-7-acetyltetrahydro-oripavine comprising Formula (IIb) as detailed in Section (I).

Several aprotic solvents are suitable for use in the hydrogenation reaction. In an exemplary iteration, the solvent is a solvent having at least one acetate moiety, preferably a C2-C5 acetate, more preferably a C2-C3 acetate, and even more preferably a C3 acetate such as isopropyl acetate. As used herein, the term "C2-C5 acetate" refers to all compounds having from two to five carbon atoms in addition to the acetate moiety. Likewise, the term "C2-C3 acetate" refers to all compounds having from two to three carbon atoms in addition to the acetate moiety.

In an exemplary embodiment, the same solvent is used in both the Diels-Alder reaction and in the hydrogenation reaction. The use of the same solvent, preferably isopropyl acetate, for both the Diels-Alder reaction and the hydrogenation reaction offers distinct advantages over the reactions run separately in different solvents. First, isolation of the Diels-Alder reaction product is not necessary, thereby saving manufacturing processing time and decreasing worker exposure to the toxic dienophile, such as methyl vinyl ketone. In addition, methyl vinyl ketone is reduced to the much less toxic ketone 2-butanone during the hydrogenation step, thereby adding a further element of safety. Also, as described below, the hydrogenation proceeds more rapidly, thereby saving manufacturing processing time. The overall processing time saved for the two steps, Diels-Alder reaction and hydrogenation, by using solvents of the present invention, preferably a solvent comprising an acetate moiety, and even more preferably isopropyl acetate, in both steps is about 40% to about 90%, preferably about 50% to about 85%, most preferably about 67% to about 80%. In addition, product of higher purity, produced in higher overall yield is obtained.

The hydrogenation catalyst may comprise catalyst that catalyzes hydrogen addition to the alkeno bridge, preferably the etheno bridge, of the endoalkeno compound, preferably the Diels-Alder adduct of Formula (II), producing the alkano, preferably ethano, bridge, such as the preferred hydrogenation product of Formula (III). In preferred embodiments the hydrogenation catalyst is a heterogeneous catalyst that is capable of being filtered from the reaction mixture. In certain preferred embodiments, the catalyst is a transition metal catalyst, optionally adsorbed onto a support such as alumina, barium sulfate, barium carbonate, calcium carbonate, carbon, and the like, and even more preferably the transition metal is a platinum-group metal, such as ruthenium, osmium, rhodium, iridium, palladium or platinum. In certain highly preferred embodiments, the platinum-group metal is palladium, optionally adsorbed onto a carbon support. Such catalysts are commercially available from suppliers such as Degussa and Engelhard.

The hydrogenation catalyst loading is preferably in the range of about 1 to about 15 mole %, preferably in the range of about 5 to about 10 mole %, most preferably in the range of about 6 to about 7 mole % of 5% palladium on charcoal.

The pressure of hydrogen gas during the hydrogenation reaction is preferably from about 10 psig to about 60 psig; more preferably from about 15 psig to about 50 psig, and even more preferably from about 20 psig to about 40 psig.

In general, the hydrogenation reaction may be conducted at a temperature that ranges from about 55° C. to about 85° C. In a preferred embodiment, the temperature of the reaction may range from about 70° C. to about 75° C.

Typically, the hydrogenation reaction is allowed to proceed for a sufficient period of time until the reaction is complete, as determined by chromatography (e.g., HPLC). In this context, a "completed reaction" generally means that the reaction mixture contains a significantly diminished amount of compounds comprising either Formula (II), (IIa) or (IIb) and a significantly increased amount of compounds comprising Formula (III). In general, however, the hydrogenation reaction time is preferably from about 4 to about 9 hours, more preferably from about 3 to about 7 hours, and even more preferably from about 5 to about 6 hours. A distinct advantage of certain of the preferred embodiments of the present process is the reduced reaction time using a solvent as described herein as the hydrogenation carrier medium, preferably as the reaction solvent. In contrast, the prior art typically indicates protic solvents for the hydrogenation reaction (e.g., alcoholic solvents, such as ethanol or isopropanol, or acidic solvents, such as acetic acid). Observed reaction time reductions using a solvent of the present invention, preferably a solvent having at least one acetate moiety, and even more preferably isopropyl acetate, compared to a protic solvent are from about 30% to about 70%, more preferably from about 40% to about 60%, and even more preferably from about 50% to about 55%.

A further distinct advantage of the solvent utilized in the hydrogenation reaction (e.g., isopropyl acetate) is that the amount of endoalkeno compound (i.e., compound comprising Formula II) not hydrogenated is significantly reduced compared to use of a protic solvent, such as acetic acid. For example, applicants have discovered that use of acetic acid typically results in greater than 1% of endoalkeno compound not hydrogenated. In comparison, use of isopropyl acetate results in complete or nearly complete hydrogenation of the endoalkeno compound. In an exemplary embodiment, the amount of endoalkeno compound not hydrogenated is less than about 0.05% by weight. In another embodiment, the amount of endoalkeno compound not hydrogenated is less than about 0.025% by weight. In an exemplary embodiment, the amount of endoalkeno compound not hydrogenated is less than about 0.01% by weight.

(b) Isolation of the Hydrogenation Reaction Product

After the hydrogenation reaction is substantially completed, the hydrogenation reaction mixture is typically concentrated to aide in the purification of the hydrogenation product. In this context, the catalyst is generally removed by filtration, and the solvent, such as isopropyl acetate, is partially removed by distillation. The amount of solvent removed can and will vary. In one embodiment, from about 50% to about 100% of the solvent is removed via distillation. In an exemplary embodiment, at least 80%, at least 85%, at least 90%, or greater than 95% of the solvent is removed via distillation.

In an exemplary iteration, after the solvent is removed from the hydrogenation reaction mixture an alkane is added. It has been found that addition of an alkane facilitates crystallization of the desired hydrogenation reaction product, such as the compound of Formula (III). The alkane may be linear, branched, or a cycloalkane. Suitable examples of alkanes include but are not limited to n-pentane, n-hexane, n-heptane, n-octane, isopentane, neopentane, isohexane, neohexane, isoheptane, neoheptane, cyclopentane, and cyclohexane. In an exemplary alternative of this embodiment, the alkane is heptane or cyclohexane. The amount of alkane added to the hydrogenation reaction mixture can and will vary without departing from the scope of the invention. In one embodiment, the amount of alkane added may range from about 0.5 to about 5 Kg for each Kg of hydrogenation product that is formed. In certain embodiments, the alkane may be added to the hydrogenation reaction mixture as it cools. In other embodiments, the alkane may be added to the hydrogenation reaction mixture while the mixture is heated, such as to a temperature from about 60° C. to about 90° C. After the addition of the alkane, however, the hydrogenation reaction mixture is typically cooled to a temperature of less than about 20° C. during the crystallization process. In an exemplary embodiment, the temperature is reduced to less than about 10° C. during the crystallization process. It has been found that this crystallization process preferably removes substantially all of the epimeric impurities (e.g., the β-epimer of either 6,14-endo-etheno-7α-acetyltetrahydro-thebaine or 6,14-endo-etheno-7α-acetyltetrahydro-oripavine), and provides the desired reaction product in crystalline form, such as crystalline 7-acetyl-6,14-endoethano-6,7,8,14-tetrahydrothebaine, preferably in a yield of least about 95% and in a purity of about 95% to about 97%, preferably a purity of about 98% to about 99%. Material of this quality is suitable for use in most applications without further purification by recrystallization. For example, according to preferred embodiments the 7-acetyl-6,14-endoethano-6,7,8,14-tetrahydrothebaine so isolated may be used directly for further processing into buprenorphine.

The compounds comprising any of Formulas (I), (II), or (III) may have a (−) or (+) with respect to the rotation of polarized light based on whether the starting material used are in the (−) or (+) opiate absolute form. More specifically, each chiral center may have an R or an S configuration. The compounds formed by the processes of the invention comprise morphinans. For purposes of illustration, the ring atoms of a morphinan compound are numbered as diagrammed below.

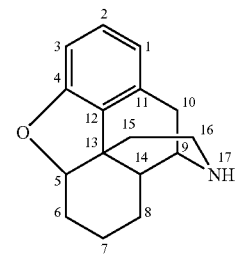

Some compounds described herein, such as compounds comprising Formula (II), may have at least six chiral centers, namely carbons C5, C6, C7, C9, C13, and C14.

The invention also encompasses use of pharmaceutically acceptable salts of any of the compounds described herein. Exemplary salts include without limitation hydrochloride, hydrobromide, phosphate, sulfate, methanesulfonate, acetate, formate, tartaric acid, maleic, malic, citrate, isocitrate, succinate, lactate, gluconate, glucuronate, pyruvate, oxalate, fumarate, propionate, aspartate, glutamate, benzoate, methyl fluoride, methyl chloride, methyl bromide, methyl iodide, and the like.

Definitions

The compounds described herein may have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements. Having described the invention in detail, it will be apparent that modifications and variations are possible without departing from the scope of the invention defined in the appended claims.

EXAMPLES

The following examples illustrate various iterations of the invention.

Example 1

Preparation of 6,14-Endo-Ethano-7-Acetyl-Tetrahydrothebaine—Hydrogenation in Acetic Acid The following example illustrates the traditional hydrogenation method, i.e., using a protic solvent. The etheno Diels-Alder adduct, 6,14-endo-etheno-7-acetyl-tetrahydrothebaine, (8.5 kg, 22.3 moles) was added portion-wise with stirring to a hydrogenation reactor containing 41 L of glacial acetic acid. After the starting material was dissolved, 223 g of platinum dioxide slurried in 1 L of acetic acid was added to the resulting solution. Hydrogenation was initiated at 15 psig hydrogen pressure at room temperature. The temperature was kept below 40° C. and the reaction was run for approximately 18 hours. The catalyst was removed by filtration through diatomaceous earth, and washed with acetic acid (3×1 L). The filtrate was added slowly to a mixture of 54 L of concentrated ammonium hydroxide, 54 kg of ice, and 42 L of chloroform. The layers were separated and the aqueous phase is extracted with chloroform (2×20 L). The organic extracts were partially dried by filtration through a thick pad of diatomaceous earth. The chloroform was removed by distillation, maintaining a pot temperature of 85-90° C., and the residual oil was mixed with 32 L of hexane. The solvent was distilled off (16 L), and the mixture was cooled to 10° C. The solid product was collected by filtration and washed with hexane (3×2 L). The crude yield was 75%. The crude product was recrystallized from ethanol (4 mL/g) in order to remove the unreacted etheno starting material and epimeric impurities. The recovery was 93%. (If the impurity content was too high, a second recrystallization from ethanol (3 mL/g) was used.)

Example 2

Preparation of 6,14Endo-Ethano-7-Acetyl-Tetrahydrothebaine—Hydrogenation in Isopropyl Acetate To determine whether hydrogenation could be performed in the presence of an aprotic solvent, the following reaction was conducted. The filtrate from a Diels-Alder reaction (in which 50 kg of thebaine was reacted with 26 kg of methyl vinyl ketone in 150 L of isopropyl acetate) was added to a hydrogenation reactor. Then, 5 kg of 5% palladium on charcoal, slurried in 10 L of isopropyl acetate, was added with stirring. Hydrogen gas was introduced at a pressure of 30 psig, and the mixture was stirred and heated to 60-70° C. for 6 hours. The catalyst was removed by filtration, and the isopropyl acetate partially removed by distillation (i.e., 130-150 L of isopropyl acetate was distilled off). Heptane, 160 L, was added, and the mixture was cooled to less than 10° C. The crystallized 6,14-endo-ethano-7-acetyl-tetrahydrothebaine was isolated by filtration in 90% yield, without the need for further purification (i.e., epimer levels were not detectable and alkene levels were less than about 0.2%). This example illustrates that hydrogenation in the presence of an aprotic solvent allowed for a shorter reaction time, with decreased impurities.

Example 3

Hydrogenation with One Distillation and Heptane Addition

The following example details a reaction conducted with a typical ratio of isopropyl acetate to starting compound. The hydrogenation reactor was purged with nitrogen and 107 kg of 6,14-endo-etheno-7-acetyl-tetrahydrothebaine and 7.2 kg of 5% palladium on carbon (wet basis) (0.067 kg/kg of starting compound) were added to the reactor. The reactor was repurged with nitrogen and 471 kg of isopropyl acetate (4.4 kg/kg of starting compound) was added. The agitator was started and the reactor was pressurized with 30 psig hydrogen and heated to 70° C. for six hours. Upon completion of the reaction, the reactor was cooled to 30° C., the hydrogen pressure was vented, and the reactor was purged with 30 psig nitrogen. The mixture (which contained ~18 wt % of the endo-ethano product in isopropyl acetate) was reheated to about 55° C. and the catalyst was removed by filtration. The hydrogenator was then rinsed with 61 kg isopropyl acetate (0.57 kg/kg of starting compound) and the two filtrates were pooled.

Isopropyl acetate was distilled from the crude filtrate under a low nitrogen purge flow by applying steam to the tank jacket. The distillation was continued until 453 kg (~139 gallons) of isopropyl acetate was collected in the distillate receiver, and the pot temperature was between 94 and 97° C. The concentrate at the end of the distillation contained about 57 wt % solution of the endo-ethano product. To this mixture, 107 kg heptane (1.0 kg/kg of starting compound) was added and the temperature was maintained between 80 and 90° C. The batch was then cooled to less than 10° C. over a four to six hour period with constant agitation (the product began to crystallize at a temperature between 70 and 80° C.). The slurry was stirred for at least one hour after the temperature reached 10° C., and then filtered or centrifuged to isolate the endo-ethano product. The solid was washed with 91 kg of heptane (0.85 kg/kg of starting compound) and dried under vacuum at 65 to 75° C. for 6 to 8 hours to give about 100 kg of 6,14-endo-ethano-7-acetyl-tetrahydrothebaine (93% isolated yield).

Example 4

Dilute Hydrogenation with Two Distillations and Heptane Additions

The following example details a reaction using a high charge ratio of isopropyl acetate to starting compound. This reaction was conducted essentially as described above in Example 3, except for two changes. First, a total of 1070 kg of isopropyl acetate was added to the reactor (i.e., a charge ratio of 10.0 kg isopropyl acetate per kg of starting compound). Second, the dilute reaction mixture (which contained ~9 wt % of product in isopropyl acetate) only had to be heated to 35 to 40° C. in order to keep the product in solution during the catalyst filtration step.

The isopropyl acetate was distilled from the filtrate as detailed in Example 3. The first distillation was continued until 880 kg (~269 gallons) of isopropyl acetate was collected in the distillate receiver. At this point, the product concentration in the batch to 30 wt %, and the pot temperature was between 90 and 93° C. Then, 503 kg of heptane (4.7 kg/kg of stating compound) was added, while maintaining the temperature between 65 and 90° C. A second distillation was then carried out until an additional 549 kg (~194 gal) of isopropyl acetate and heptane were distilled, and the pot temperature increased to between 95 and 98° C. After completing the second distillation, an additional 214 kg heptane (2.0 kg/kg of starting compound) was added while maintaining the temperature between 80 and 90° C. At this point, the batch composition was roughly 20 wt % product, 7 wt % isopropyl acetate and 73 wt % heptane. The batch was then gradually cooled to less than 10° C. over a four to six hour period, and the slurry was stirred for at least one hour after the temperature reached 10° C. The slurry was then filtered or centrifuged to isolate the endo-ethano product. The solid was washed with 91 kg heptane (0.85 kg/kg of starting material) and dried under vacuum at 65 to 75° C. for 6 to 8 hours to give about 100 kg of 6,14-endo-ethano-7-acetyl-tetrahydrothebaine (93% isolated yield).

What is claimed is:
1. A process for the preparation of a compound of Formula (III), the process comprising a first reaction that comprises contacting a compound of Formula (I) with an aprotic solvent and a dienophile to form a compound of Formula (II), and then a second reaction that comprises contacting the compound of Formula (II) with a catalyst, hydrogen, and the aprotic solvent to form a compound of Formula (III) according to the following reaction scheme:

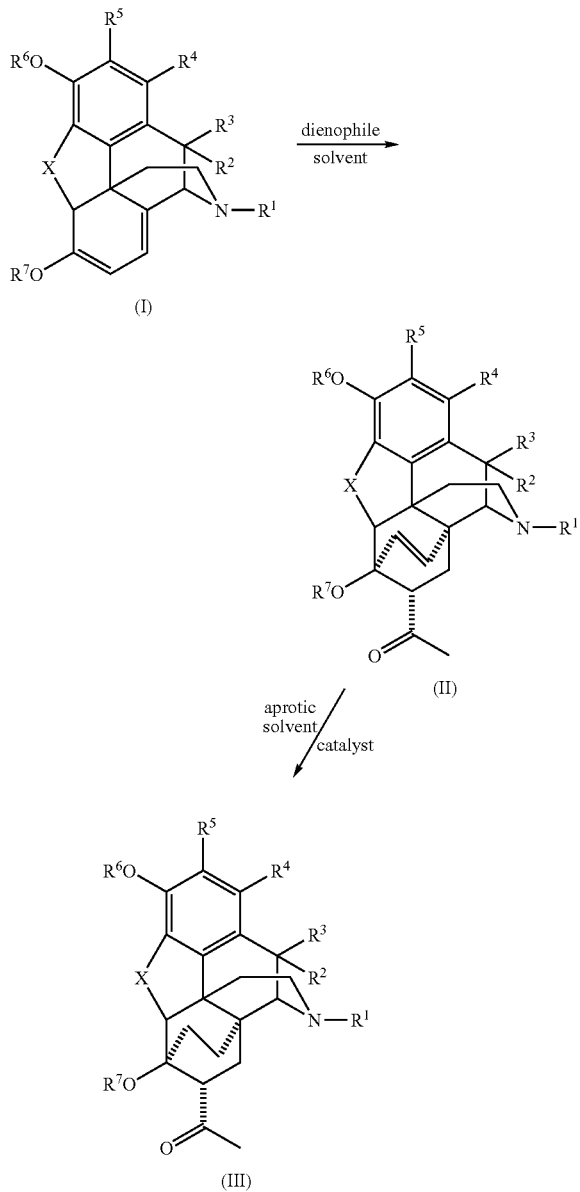

wherein:
$R^1$ and $R^8$ are independently selected from the group consisting of hydrocarbyl and substituted hydrocarbyl;
$R^2$ and $R^3$ are independently selected from the group hydrogen, hydrocarbyl and substituted hydrocarbyl;
$R^4$ and $R^5$ are independently selected from the group consisting of hydrogen, hydrocarbyl, substituted hydrocarbyl, halogen, {—}OH, {—}NH$_2$, {—}SH, {—}SR$^8$, and {—}OR$^8$;
$R^6$ and $R^7$ are independently selected from the group consisting of hydrogen, a protecting group, hydrocarbyl, and substituted hydrocarbyl; and
X is oxygen, and
wherein the first reaction and the second reaction are both conducted in a one-pot process; and the aprotic solvent used for the first reaction and the aprotic solvent for the second reaction are the same.

2. The process of claim 1, wherein the aprotic solvent comprises a compound comprising an acetate moiety, and the catalyst is a transition metal catalyst.

3. The process of claim 2, wherein the compound comprising the acetate moiety comprises an acetate having from two carbon atoms to five carbon atoms.

4. The process of claim 1, wherein the aprotic solvent comprises isopropyl acetate.

5. The process of claim 1, wherein the aprotic solvent comprises isopropyl acetate, the catalyst is a palladium catalyst adsorbed onto a carbon support, and the hydrogenation reaction is conduced at a temperature from about 65° C. to about 85° C.

6. The process of claim 1, wherein less than 0.5% by weight of the morphinan of Formula (II) remains in the reaction mixture after the hydrogenation reaction is completed; and the yield of the morphinan of Formula (III) is greater than 97%.

7. The process of claim 1, wherein the dienophile is methyl vinyl ketone, and the first reaction is conducted at a temperature ranging from about 70° C. to about 100° C. the aprotic solvent comprises isopropyl acetate, the catalyst is a palladium catalyst adsorbed onto a carbon support, and the second reaction is conduced at a temperature from about 65° C. to about 85° C.

8. The process of claim 1, wherein the compound of Formula (III) is selected from the group consisting of 6,14-endo-etheno-7-acetyltetrahydro-oripavine, and 6,14-endo-etheno-7-acetyltetrahydro-thebaine.

9. The process of claim 1, further comprising removal of at least a portion of the isopropyl acetate after the second reaction is substantially complete followed by the addition of an alkane as the second reaction is cooled to less than 20° C.

* * * * *